(12) United States Patent
Dace et al.

(10) Patent No.: US 8,142,440 B2
(45) Date of Patent: Mar. 27, 2012

(54) TRANSVERSE CENTERING TOOL WITH PIN PLACEMENT GUIDES

(75) Inventors: Mark C. Dace, Collierville, TN (US); Richard G. Fessler, Winnetka, IL (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 670 days.

(21) Appl. No.: 12/271,357

(22) Filed: Nov. 14, 2008

(65) Prior Publication Data

US 2010/0125277 A1     May 20, 2010

(51) Int. Cl.
*A61B 17/60* (2006.01)
*A61B 17/90* (2006.01)

(52) U.S. Cl. .......................................................... 606/96

(58) Field of Classification Search ................. 606/96, 606/206, 207
See application file for complete search history.

(56) References Cited

U.S. PATENT DOCUMENTS

| | | | |
|---|---|---|---|
| 5,674,296 A | 10/1997 | Bryan et al. | |
| 5,865,846 A | 2/1999 | Bryan et al. | |
| 6,379,364 B1 | 4/2002 | Brace et al. | |
| 6,949,105 B2 | 9/2005 | Bryan et al. | |
| 7,033,362 B2 | 4/2006 | McGahan et al. | |
| 7,081,119 B2 | 7/2006 | Stihl | |
| 7,179,262 B2 | 2/2007 | Bryan et al. | |
| 2001/0000532 A1 | 4/2001 | Michelson | |
| 2002/0161446 A1 | 10/2002 | Bryan et al. | |
| 2002/0198533 A1 | 12/2002 | Geisler et al. | |
| 2003/0032962 A1 | 2/2003 | McGahan et al. | |
| 2005/0059976 A1 | 3/2005 | Bryan et al. | |
| 2006/0085077 A1 | 4/2006 | Cook et al. | |
| 2006/0195109 A1 | 8/2006 | McGahan et al. | |
| 2007/0016217 A1 | 1/2007 | Dinville | |
| 2007/0118224 A1 | 5/2007 | Shah et al. | |

*Primary Examiner* — Bruce E Snow (57) ABSTRACT

A centering tool for transverse centering between an upper vertebra and a lower vertebra is disclosed. The centering tool comprises a support portion having a proximal end and a distal end, two handles, and two pin placement guides, each guide having a hollow cylinder shape for the placement of a drill or pin on each of the upper and lower vertebrae. The two handles each have a proximal end and a distal end, wherein the proximal end of each handle is connected to the proximal end of the support portion, and the distal end of each handle ultimately contact the uncular joint of one of the vertebrae when centering is achieved. Preferably, each handle has a spring that biases the handle in a closed position so that the distal portions of both handles abut each other in a resting or closed position.

20 Claims, 7 Drawing Sheets

TRANSVERSE CENTERING TOOL WITH PIN PLACEMENT GUIDES

TECHNICAL FIELD

The invention relates to methods and associated instrumentation for stereotactically locating the site for a prosthetic implant in a body, and in particular, methods and associated instrumentation for stereotactically locating and preparing the site for an intervertebral endoprosthesis.

BACKGROUND

The proper location of any endoprosthetic implant is a key element for the success of the implantation procedure in improving patient quality of life. In spinal implants, for example, proper placement of the endoprosthesis ensures, among other benefits, that the patient will enjoy the full range of motion offered by the implant.

The use of intervertebral implants (arthroplasty) has, in recent years, attained increasing acceptance as a preferable alternative to spinal fusion (arthrodesis) as a method for treating patients where discectomy is indicated. This is in part due to recent advances in implant technology, and in part due to the increasing appreciation of the advantages provided by implantation, including increased range of motion, decreased post-operative damage to adjacent intervertebral discs (which can result from the decreased range of motion at the level of the fusion), decreased risk of harvest site morbidity, etc. This increasing acceptance seems likely to continue for the foreseeable future, and more and more implantation procedures will likely be performed.

Surgical implantation of prostheses into the intervertebral space may be done using a posterior approach or an anterior approach. The posterior approach has the disadvantage of requiring dissection of muscle tissue of the back, which causes patient discomfort and increased healing time. An anterior surgical approach is often preferable for this and other reasons, and is quite practical for implantation between cervical vertebrae, in particular. Irrespective of the surgical approach, precisely locating the desired implant position, and precise positioning of cavity preparation tools and of the implant at that location are essential. Errors in positioning of the implant or in positioning of the devices used to prepare the intervertebral space to receive the implant can be catastrophic to the patient, given the proximity of the surgical site to the spinal cord, vertebral arteries and other such critical structures.

Similar considerations apply in other areas of surgery, in particular in neurosurgery. For example, during surgery on the brain, the surgeon often anchors a frame to the sides of the patient's head, which provides constant reference points during surgery, irrespective of how the patient's head or neck is positioned or moved during the procedure. This level of stereotactic precision in location and placement also is desirable for other medical and surgical procedures, such as in spinal surgery, where the margin for error is very small due to the proximity to the spinal cord and other neuro and vascular structures. In most procedures used for spinal surgery, however, as well as surgery to other body parts, it is impossible (or at least impracticable or undesirable) to secure an external frame to the patient's skeleton or soft tissues to provide constant reference points.

Electronic systems exist for stereotactic positioning of medical instruments during surgical procedures. These systems are extremely expensive, however, requiring significant computing power, are highly complex, require specialized software, and are not always available, particularly in smaller health care systems or in less developed countries.

Accordingly, there remains a need in the art for a method and apparatus for stereotactically locating targeted implantation positions, for precisely positioning tools for preparing the implantation site, and for precisely inserting the implant in the desired position that is simple, safe, that does not require expensive electronic or computerized tracking of medical instrumentation, and that can be used with conventionally available imaging technologies.

Examples of procedures for introducing intervertebral implants are described in U.S. Pat. Nos. 5,674,296, 5,865,846, 6,949,105, and 7,179,262, the entire contents of each of which are hereby incorporated by reference. These patents generally disclose the steps of determining which size and shape of prosthetic vertebral body disc a patient needs and implanting that prosthetic disc into the patient's spine.

More specifically, the surgeon or medical technician determines the size, shape, and nature of a patient's damaged vertebral body by viewing images of the patient's spine, such as radiographs, CT and/or other MRI scans. Based upon that information, an appropriate size of prosthetic disc is constructed by a specialized laboratory in conformity with the information provided by the surgeon or medical technician. The prosthetic discs are described as having concaval-convex elements.

Before the implantation of an artificial disc, the patient is prepared and the damaged natural spinal disc material is removed. The surgeon forms holes in the bone structure using a measuring instrument centered in the excavated natural intervertebral disc space. These holes may be tapped to form female threads and anchors are implanted therein to a platform of reference points with respect to the patient's spine. A bone surface machining jig is then affixed to the anchors and used to form the desired concave surfaces on the inferior and superior surfaces of opposing vertebral bodies, using a milling head or bit of predetermined size.

After the bone surface machining jig is removed, a prosthetic disc, having corresponding concaval surfaces, is inserted between the distracted and milled vertebral bodies. The concaval-convex elements are then attached by the same anchors to the bone, insuring a mate between the bone surface and the concaval-convex elements.

While these methods are certainly sufficient to achieve a successful intervertebral implantation, there remains a need for improved techniques and instruments that provide even more precise localization, such as improved stereotactic location of the desired site of the implant, the precision positioning of milling, burring, and other tools and instruments for conducting the procedure, and the implantation of the endoprosthesis into the prepared site.

Specifically, however, the purpose of the present invention is to locate the precise transverse center of vertebrae inferior and superior to an artificial disc implant, but the concept can be applied generally to other areas.

SUMMARY

A centering tool for transverse centering between an upper vertebra and a lower vertebra is disclosed. The centering tool comprises a support portion having a proximal end and a distal end, two handles, and two pin placement guides, each guide having a hollow cylinder shape for the placement of a drill or pin on each of the upper and lower vertebrae. The two handles each have a proximal end and a distal end, wherein the proximal end of each handle is connected to the proximal end of the support portion, and the distal end of each handle ultimately contact the uncular joint of one of the vertebrae when centering is achieved. Preferably, the handles contain a spring in between them to bias them toward each other in a closed position so that the distal portions of both handles abut each other in a resting or closed position.

In some embodiments, the support portion further comprises a knob, for after the two handles are in desired position, the knob can be used to maintain the two handles in the desired position. In other embodiments, the distal end of each handle further comprises a tip that extends outwardly from the support portion to contact the uncular joint. In yet other embodiments, on its proximal end the support portion further comprises a bubble level to help establish when the centering tool is in the vertical orientation of the axial or sagittal plane.

A method of transverse centering between an upper vertebra and a lower vertebra after a discectomy has been performed also is disclosed. The method comprises the steps of providing the centering tool disclosed herein, placing the distal ends of the two handles of the centering tool in between the upper and lower vertebrae, squeezing toward each other the two proximal ends of the two handles, and once each of the distal ends of the two handles contact the uncular joint of the vertebra, centering has been achieved.

In certain techniques, the method further comprises the step after each of the distal ends of the two handles have contacted the uncular joint, tightening the knob to maintain the two handles in such a centered position. In other techniques, the method further comprises the step of after maintaining the two handles in desired position, placing a pin through the pin placement guides and into each of the upper and lower vertebrae to mark the center of each of the upper and lower vertebrae. In such technique, the method may further comprises the step of after maintaining the two handles in desired position, placing a drill through the pin placement guides and into each of the upper and lower vertebrae to drill a hole into the center of each of the upper and lower vertebrae. In addition, the method may further comprises the step of after drilling a hole in each of the upper and lower vertebrae, placing a bit for retraction of both the upper and lower vertebrae. In other techniques, the method may comprise an additional step of prior to using the centering tool to achieve transverse centering, using a bubble level to help establish that the centering tool is in the vertical orientation of the axial plane.

Additional aspects and features of the present disclosure will be apparent from the detailed description and claims as set forth below.

DETAILED DESCRIPTION

For the purpose of promoting an understanding of the principles of the present disclosure, reference is made to the specific embodiments illustrated in the drawings, and specific language is used to describe the embodiments. It is nevertheless understood that no limitation of the scope of the present disclosure is intended. Any alterations and further modifications of the described embodiments, and any further applications of the principles of the present disclosure as described herein, are fully contemplated, as would occur to one skilled in the art to which the invention relates.

As stated above, the purpose of the present invention is to locate the precise transverse center of vertebrae inferior and superior to an implant. In particular, the present invention allows for single-step centering and placing of a pin on each of these adjacent vertebrae for vertebral body retraction. Thus, an implant can be inserted in its properly centered location so that the load of the spine and structures above it are properly centered and not unevenly balanced.

Figure 1:
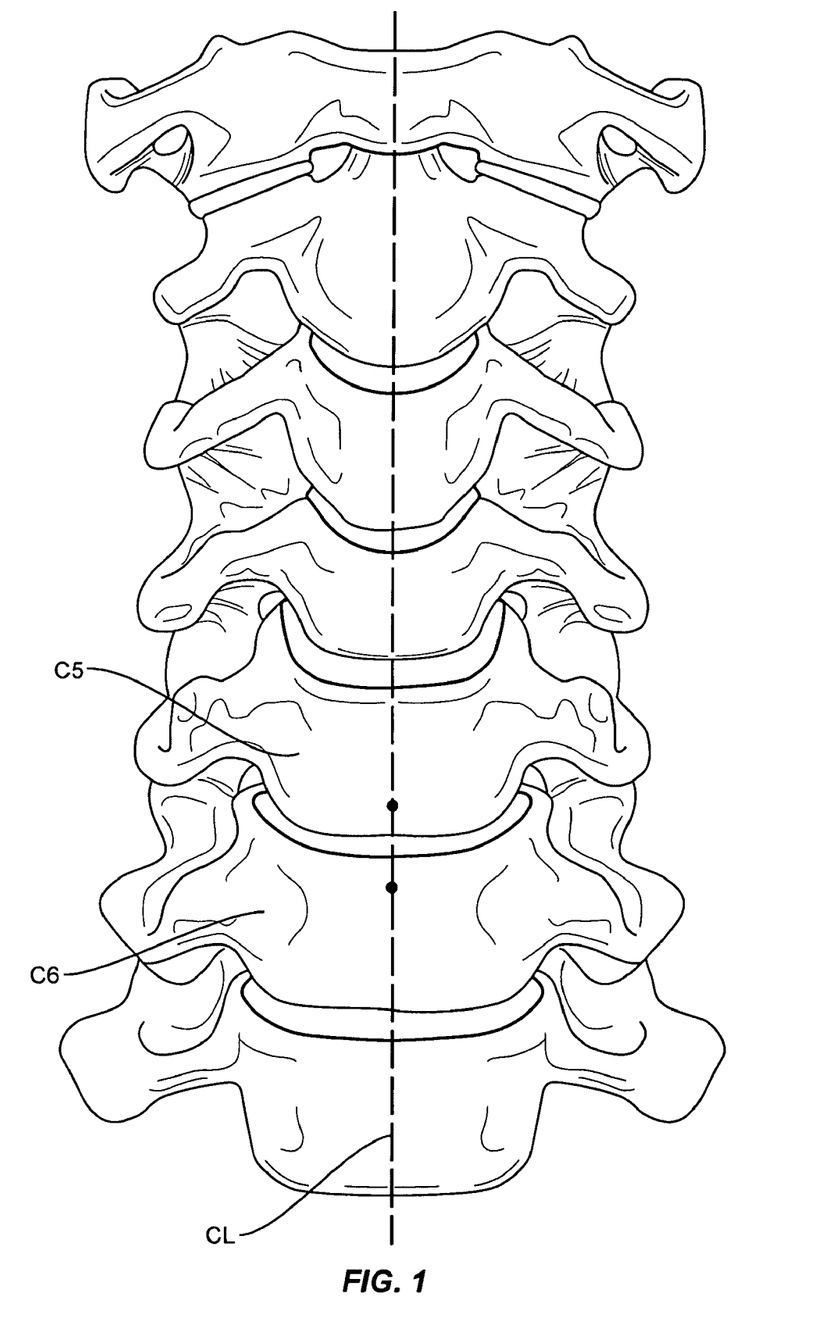
FIG. 1 shows a frontal view of a section of cervical spine.

FIG. 1 shows a frontal view of a section of cervical spine. In particular, FIG. 1 shows cervical vertebral sections C1 through C6 after the disc between vertebral sections C5 and C6 has been removed. FIG. 1 also shows a Centerline CL that illustrates the midline of the vertebral sections C5 and C6, the location of which is the ultimate goal of the present invention.

Figure 2:
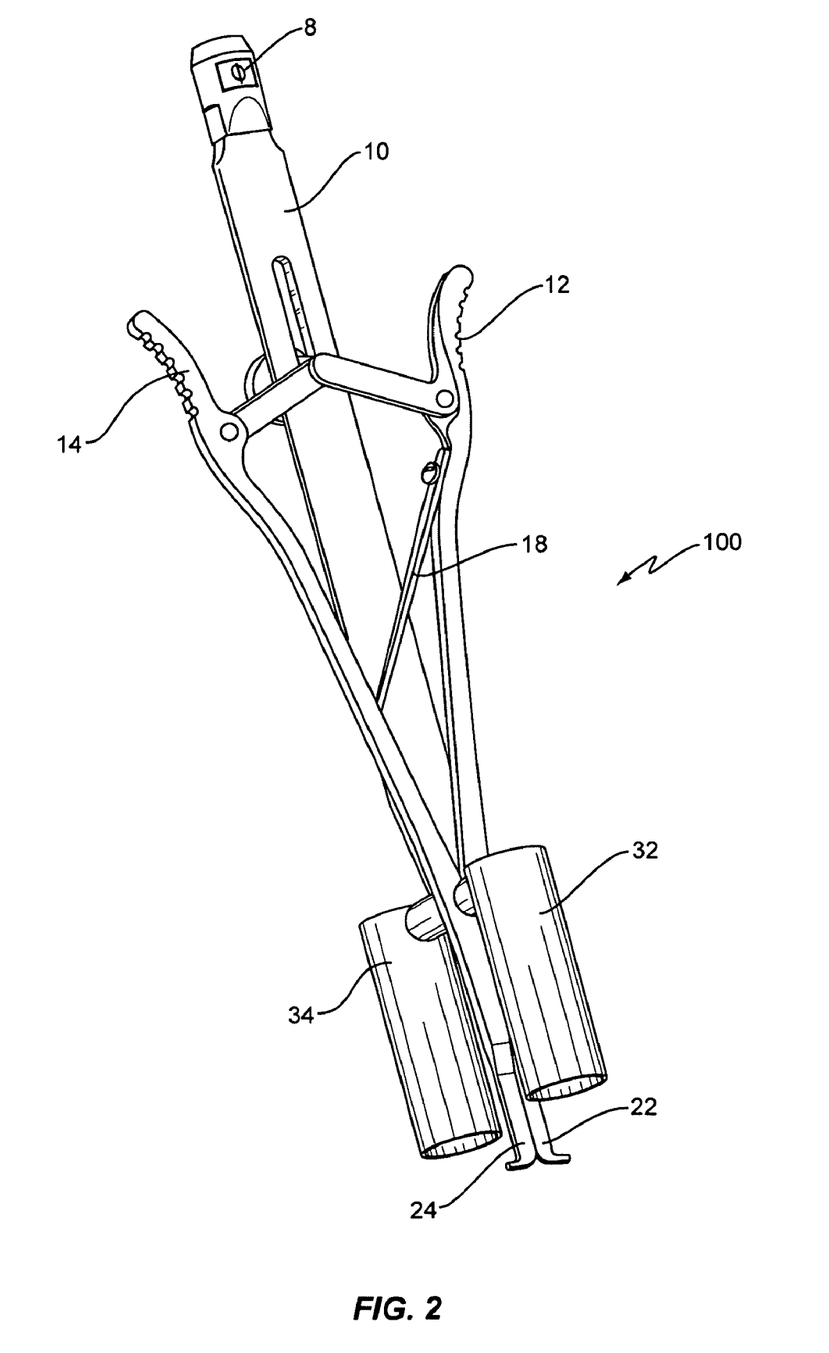
FIG. 2 shows an isometric view of the transverse centering tool of the present invention.

FIG. 2 shows an isometric view of the transverse centering tool with pin placement guides of the present invention. The transverse centering tool 100 comprises a support portion 10, two scissor handles (or arms) 12 and 14, each having distal ends 22 and 24, and pin placement guides 32 and 34 (or barrels). The pin placement guides 32 and 34 each have the shape of hollow cylinders. The support portion 10 of the transverse centering tool 100 is fitted with a bubble level 8 on the top or distal portion of the support portion 10, which helps one know when the tool 100 is vertical in the axial plane when the patient is lying face up on an operating table. The level also may be used to establish vertical orientation in the sagittal plane if necessary for the specific surgical technique.

Figure 3:
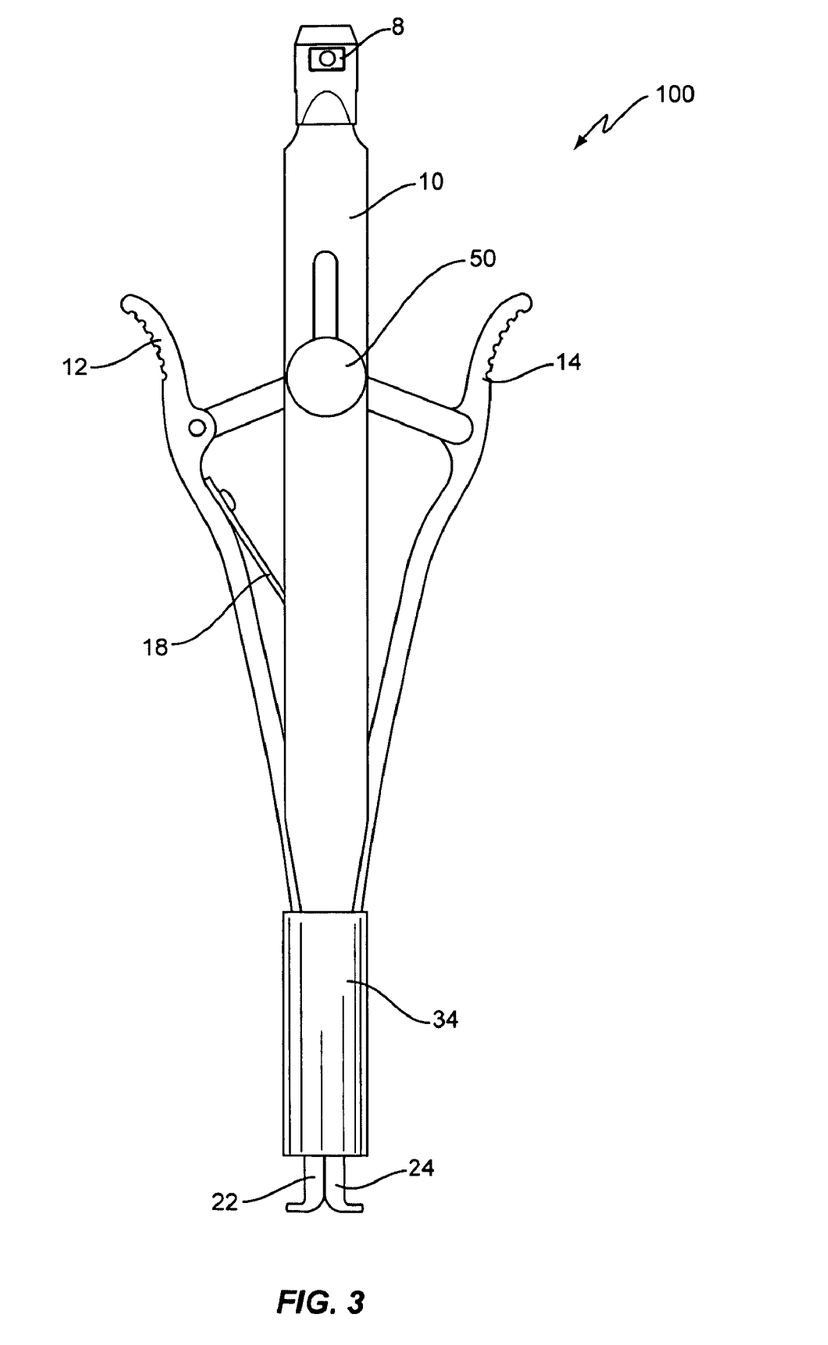
FIG. 3 shows a side view of the transverse centering tool of the present invention.
Figure 4:
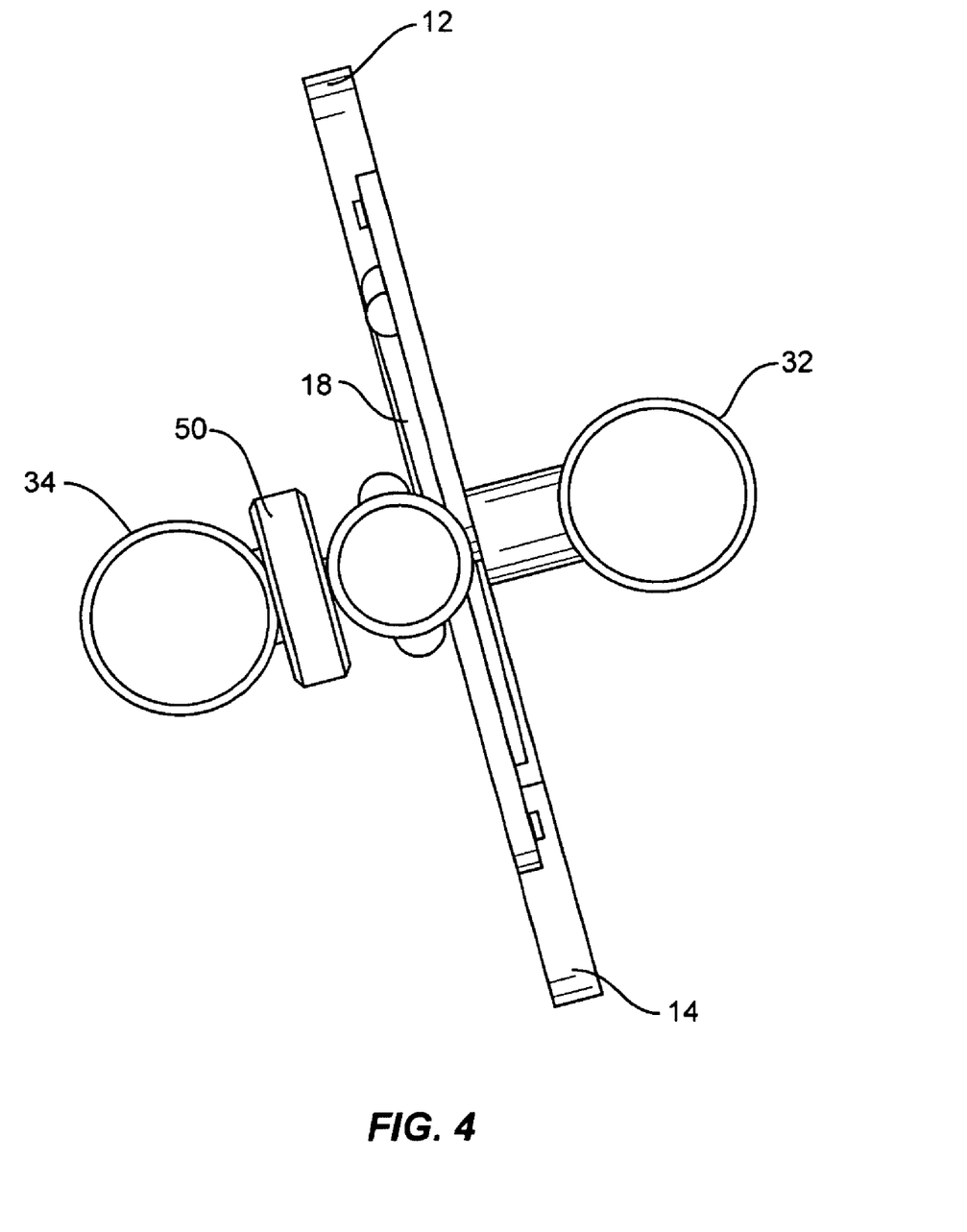
FIG. 4 shows an elevation view of the transverse centering tool of the present invention.

FIG. 3 shows a side view, while FIG. 4 shows an elevation view of the transverse centering tool 100 of the present invention. The scissor handles 12 and 14 are spring-loaded to be biased to be positioned as shown in FIGS. 2 and 3 while in its natural, un-stressed position. There is a spring 18 in between the handles 12 and 14 that biases the handles 12 and 14 against each other in its resting position. As shown in the figures, the spring 18 is a flat spring, although another type of spring or springs are possible.

Figure 5:
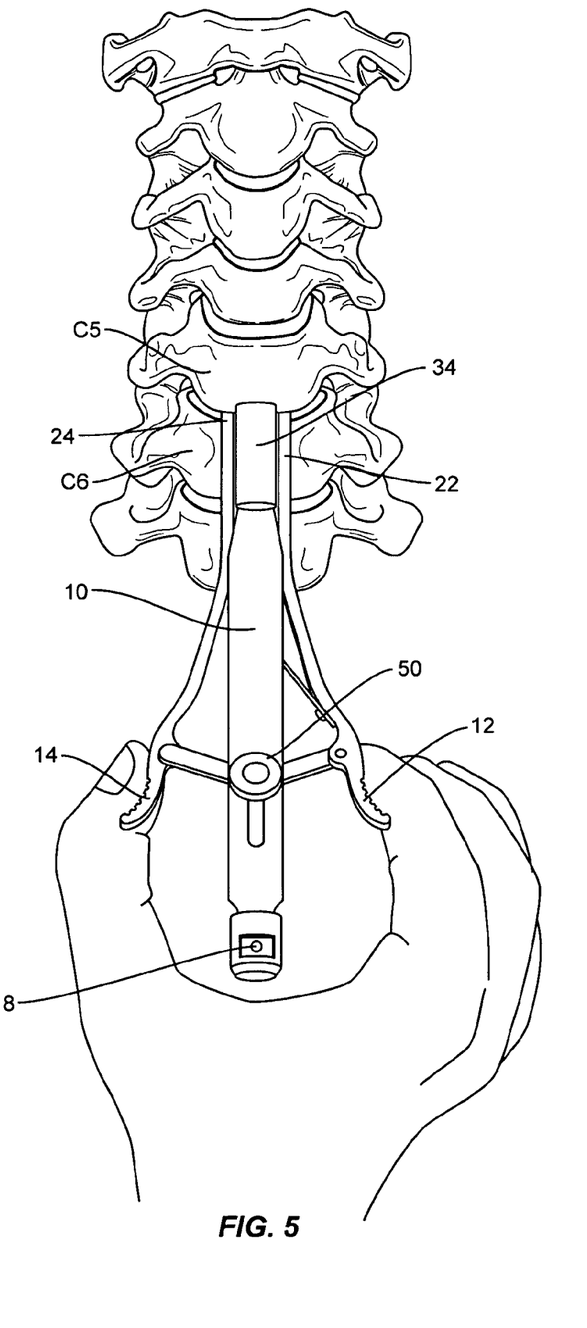
FIG. 5 shows the transverse centering tool of the present invention in use.
Figure 6:
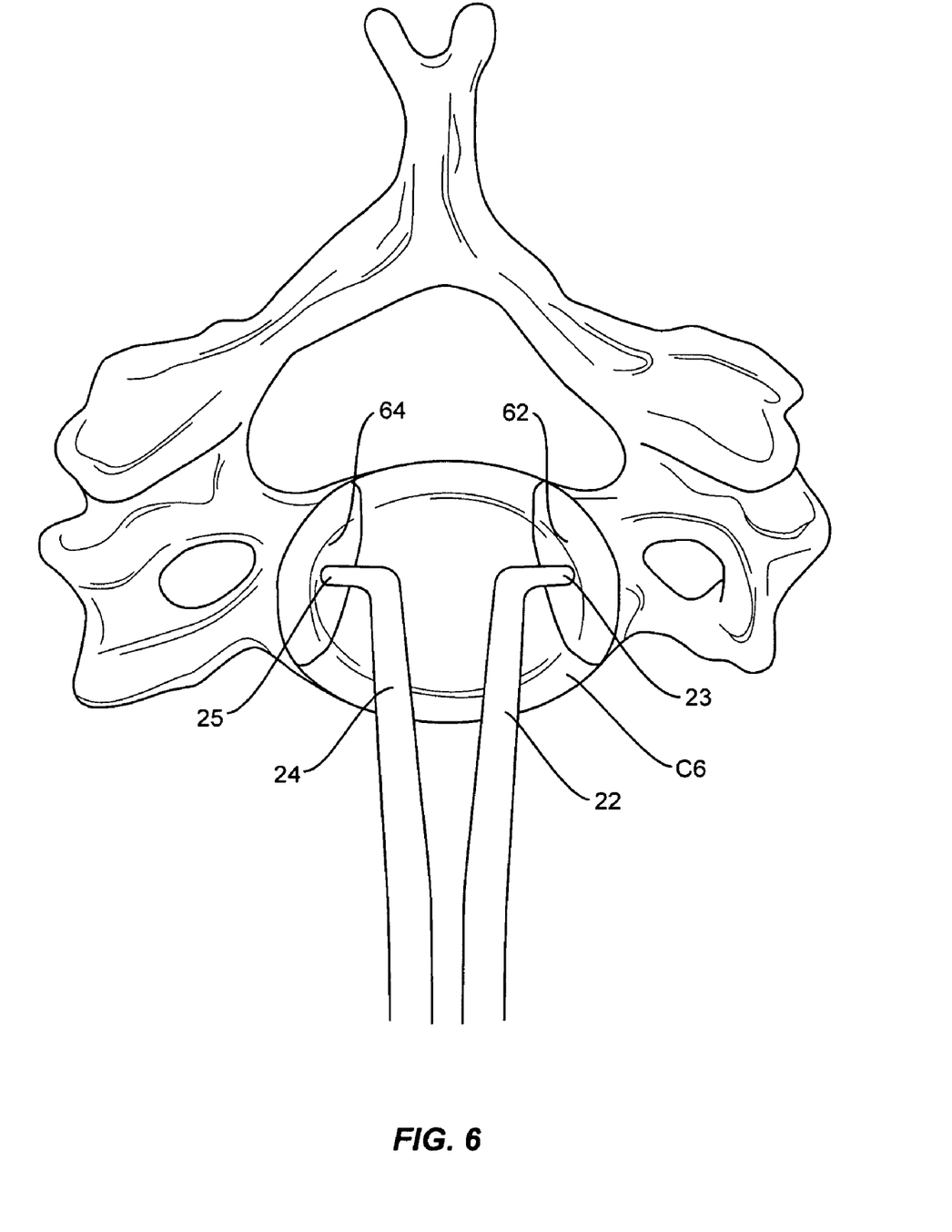
FIG. 6 shows only the tips of the distal ends of the scissor handles of the transverse centering tool of the present invention in cooperation with vertebra C5.

FIG. 5 shows the transverse centering tool 100 of the present invention in use. After discectomy, the distal ends 22 and 24 of the transverse centering tool 100 are placed between the endplates of vertebral sections C5 and C6 of FIG. 1. As shown in FIG. 5, one then exerts pressure inward on the proximal ends of the scissor handles 12 and 14. This pressure causes the distal ends 22 and 24 of the scissor handles 12 and 14 to separate, as shown in FIG. 5. The distal ends 22 and 24 of the scissor handles 12 and 14 separate until they contact the intersections of the annulus fibrosus and the uncinate process (or uncular joint) on each side of the intervertebral process. A close-up view of this area of vertebra C5 is shown in FIG. 6, but only showing the tips of the distal ends 23 and 25 of the scissor handles 22 and 24, respectively, of the transverse centering tool 100 of the present invention in cooperation with vertebra C5, i.e., without the pin placement guides 32 and 34 for better visibility. As more clearly seen in FIG. 6, the tips 23 and 25 of the distal ends 22 and 24 of the scissor handles 12 and 14 are contacting the intersections 62 and 64, respectively, of the annulus fibrosus and the uncinate process on each side of the intervertebral process. As shown, the tips 23 and 25 of the distal ends 22 and 24 of each handle 12 and 14 extend outwardly from the support portion 10.

After the tips of the distal ends 22 and 24 of the scissor handles 12 and 14 are in contact with the intersections 62 and 64, respectively, of the annulus fibrosus and the uncinate process on each side of the intervertebral process, one knows the transverse centering tool 100 is in alignment or centered on the midline CL between vertebrae C5 and C6, as shown in FIG. 1. At this stage, the knob 50 is tightened so that the position of the scissor handles 12 and 14 are maintained.

Figure 7:
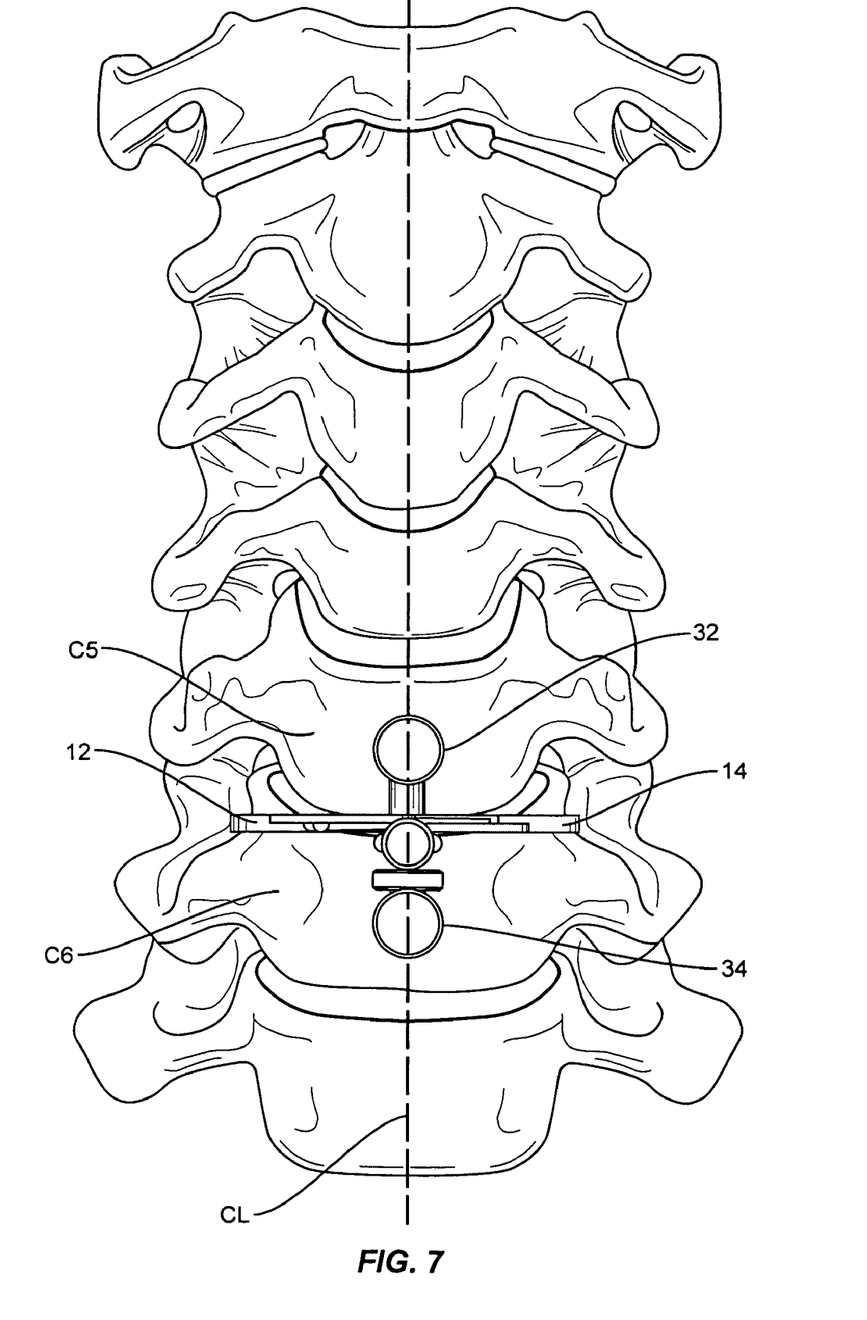
FIG. 7 shows an elevation view of the transverse centering tool of the present invention in cooperation with a section of cervical spine after the transverse centering tool has been used to locate the midline between vertebrae C5 and C6.

At the point that centering has been achieved, and the handles 12 and 14 have been stabilized, drilling can be accomplished. The midline CL seen in FIG. 1 also is seen in FIG. 7, along with the transverse centering tool 100 in an elevation view. In particular, FIG. 7 shows the pin placement guides 32 and 34 centered along the midline CL on vertebrae C5 and C6, respectively. Thus, drills can be inserted into the pin placement guides 32 and 34 so that holes that are transversely-centered on the vertebrae can be drilled in each vertebra. Alternatively, transversely-centered pins can be placed or punched for some other form of affixation. Ultimately, at this time, it is intended that one can use these center marks for pins or drill holes for both retraction and for proper placement of an implant. As described above, an implant can be inserted in its properly centered location so that the load of the spine and structures above it are properly centered and not unevenly balanced. Thus, the transverse centering tool 100 of the present invention locates the precise transverse center of vertebrae inferior and superior to an implant. After discectomy, the transverse centering tool 100 can do this in a single-step.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure. It is understood that all spatial references, such as "horizontal," "vertical," "top," "upper," "lower," "bottom," "left," and "right," are for illustrative purposes only and can be varied within the scope of the disclosure. In the claims, means-plus-function clauses are intended to cover the structures described herein as performing the recited function and not only structural equivalents, but also equivalent structures.

What is claimed:

1. A centering tool for transverse centering between an upper vertebra and a lower vertebra, the tool comprising:
    a support portion having a proximal end and a distal end;
    two handles, each having a proximal end and a distal end, wherein the proximal end of each handle is connected to the proximal end of the support portion, and the distal end of each handle ultimately contact an uncular joint of one of the vertebrae when centering is achieved; and
    two pin placement guides having a proximal end and a distal end, fixedly attached to the distal ends of each of the two handles, each guide having a hollow cylinder shape for the placement of a drill or pin on each of the upper and lower vertebrae being centered along the midline CL on the vertebrae.

2. The centering tool of claim 1, wherein the handles are biased in a closed position so that the distal portions of both handles abut each other in a resting or closed position.

3. The centering tool of claim 2, wherein a spring biases the handles in the closed position.

4. The centering tool of claim 3, wherein the spring is a flat spring.

5. The centering tool of claim 1, wherein: the support portion further comprises a knob, for after the two handles are in desired position, the knob can be used to maintain the two handles in the desired position.

6. The centering tool of claim 1, wherein: the distal end of each handle further comprises a tip that extends outwardly from the support portion to contact the uncular joint.

7. The centering tool of claim 1, wherein: the support portion further comprises a bubble level to help establish when the centering tool is in the vertical orientation of the axial plane.

8. A method of transverse centering between an upper vertebra and a lower vertebra after a discectomy has been performed, the method comprising the steps of:
    providing a centering tool having: a support portion having a proximal end and a distal end; two handles, each having a proximal end and a distal end, wherein the proximal end of each handle is connected to the proximal end of the support portion, and the distal end of each handle ultimately contact an uncular joint of one of the vertebrae when centering is achieved; and two pin placement guides having a proximal end and a distal end, fixedly attached to the distal ends of each of the two handles, each guide having a hollow cylinder shape for the placement of a drill or pin on each of the upper and lower vertebrae being centered along the midline CL on the vertebrae;
    placing the distal ends of the two handles of the centering tool in between the upper and lower vertebrae;
    squeezing toward each other the two proximal ends of the two handles;
    once each of the distal ends of the two handles contact the uncular joint of the vertebra, centering has been achieved.

9. The method of claim 8, wherein the centering tool further comprises a knob, and the method further comprising a step after each of the distal ends of the two handles have contacted the uncular joint, tightening the knob to maintain the two handles in such a centered position.

10. The method of claim 9 further comprising a step of after maintaining the two handles in desired position, placing a pin through the pin placement guides and into each of the upper and lower vertebrae to mark the center of each of the upper and lower vertebrae.

11. The method of claim 10 further comprising a step of after maintaining the two handles in desired position, placing a drill through the pin placement guides and into each of the upper and lower vertebrae to drill a hole into the center of each of the upper and lower vertebrae.

12. The method of claim 11 further comprising a step of after drilling a hole in each of the upper and lower vertebrae, placing a bit for retraction of both the upper and lower vertebrae.

13. The method of claim 8, wherein the distal end of each handle further comprises a tip that extends outwardly from the support portion so that it is the tip of the distal end of each handle that contacts the uncular joint when centering is achieved.

14. The method of claim 13, wherein the centering tool further comprises a knob, and the method further comprising a step after each of the tips of each distal end of the two handles have contacted the uncular joint, tightening the knob to maintain the two handles in such a centered position.

15. The method of claim 14 further comprising a step of after maintaining the two handles in desired position, placing a pin through the pin placement guides and into each of the upper and lower vertebrae to mark the center of each of the upper and lower vertebrae.

16. The method of claim 15 further comprising a step of after maintaining the two handles in desired position, placing a drill through the pin placement guides and into each of the upper and lower vertebrae to drill a hole into the center of each of the upper and lower vertebrae.

17. The method of claim 8, wherein the support portion of the centering tool further comprises a bubble level, and the method further comprising a step prior to squeezing the two handles of the centering tool toward each other, using the bubble level to help establish that the centering tool is in the vertical orientation of the axial plane.

18. A method of transverse centering between an upper vertebra and a lower vertebra after a discectomy has been performed, the method comprising the steps of:
providing a centering tool having: a support portion having a proximal end and a distal end, wherein the proximal end has a bubble level; two handles, each having a proximal end and a distal end, wherein the proximal end of each handle is connected to the proximal end of the support portion, and the distal end of each handle ultimately contact the uncular joint of one of the vertebrae when centering is achieved; and two pin placement guides having a proximal end and a distal end, fixedly attached to the distal ends of each of the two handles, each guide having a hollow cylinder shape for the placement of a drill or pin on each of the upper and lower vertebrae being centered along the midline CL on the vertebrae;
placing the distal ends of the two handles of the centering tool in between the upper and lower vertebrae;
using the bubble level to help establish that the centering tool is in the vertical orientation of the axial plane;
after it has been established that the centering tool is in the vertical orientation of the axial plane, squeezing toward each other the two proximal ends of the two handles;
once each of the distal ends of the two handles contact the uncular joint of the vertebra, centering has been achieved.

19. The method of claim 18, wherein the centering tool further comprises a knob, and the method further comprising a step after each of the distal ends of the two handles have contacted the uncular joint, tightening the knob to maintain the two handles in such a centered position.

20. The method of claim 19 further comprising a step of after maintaining the two handles in desired position, placing a pin through the pin placement guides and into each of the upper and lower vertebrae to mark the center of each of the upper and lower vertebrae.

* * * * *